United States Patent
Narayanan et al.

(10) Patent No.: US 10,188,100 B2
(45) Date of Patent: Jan. 29, 2019

(54) MATRIX COMPOSITION FOR DELIVERY OF HYDROPHOBIC ACTIVES

(76) Inventors: Kolazi S. Narayanan, Wayne, NJ (US); Domingo Jon, New York, NY (US); Jayanti V. Patel, Elmwood Park, NJ (US)

( * ) Notice: Subject to any disclaimer, the term of this patent is extended or adjusted under 35 U.S.C. 154(b) by 0 days.

(21) Appl. No.: 13/521,138

(22) PCT Filed: Jan. 10, 2011

(86) PCT No.: PCT/US2011/020679
§ 371 (c)(1),
(2), (4) Date: Nov. 16, 2012

(87) PCT Pub. No.: WO2011/085310
PCT Pub. Date: Jul. 14, 2011

(65) Prior Publication Data
US 2013/0196853 A1 Aug. 1, 2013

Related U.S. Application Data

(60) Provisional application No. 61/293,759, filed on Jan. 11, 2010.

(51) Int. Cl.
| | |
|---|---|
| *A61K 8/06* | (2006.01) |
| *A61K 47/16* | (2006.01) |
| *A01N 25/00* | (2006.01) |
| *A01N 25/02* | (2006.01) |
| *A61K 8/42* | (2006.01) |
| *A61K 8/55* | (2006.01) |
| *A61K 8/86* | (2006.01) |
| *A61K 9/00* | (2006.01) |
| *A61K 9/10* | (2006.01) |
| *A61K 9/107* | (2006.01) |
| *A61K 47/10* | (2017.01) |
| *A61K 47/14* | (2017.01) |
| *A61K 47/20* | (2006.01) |
| *A61K 47/22* | (2006.01) |
| *A61K 47/34* | (2017.01) |
| *A61Q 19/00* | (2006.01) |
| *C09K 3/00* | (2006.01) |
| *A01N 37/18* | (2006.01) |

(52) U.S. Cl.
CPC .............. *A01N 25/00* (2013.01); *A01N 25/02* (2013.01); *A01N 37/18* (2013.01); *A61K 8/06* (2013.01); *A61K 8/42* (2013.01); *A61K 8/556* (2013.01); *A61K 8/86* (2013.01); *A61K 9/0014* (2013.01); *A61K 9/10* (2013.01); *A61K 9/107* (2013.01); *A61K 9/1075* (2013.01); *A61K 47/10* (2013.01); *A61K 47/14* (2013.01); *A61K 47/16* (2013.01); *A61K 47/20* (2013.01); *A61K 47/22* (2013.01); *A61K 47/34* (2013.01); *A61Q 19/00* (2013.01); *C09K 3/00* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 4,506,051 A | 3/1985 | Rance | |
| 5,206,225 A * | 4/1993 | Horstmann | A01N 25/02 514/383 |
| 5,425,955 A * | 6/1995 | Narayanan | 424/405 |
| 5,766,615 A | 6/1998 | Narayanan | |
| 6,255,253 B1 * | 7/2001 | Foerster et al. | 504/363 |
| 6,716,949 B2 | 4/2004 | Ganapathiappan | |
| 9,730,439 B2 * | 8/2017 | Narayanan | C08K 5/17 |
| 2002/0028182 A1 | 3/2002 | Dawson et al. | |
| 2004/0235668 A1 * | 11/2004 | Abribat | A01N 25/04 504/363 |
| 2007/0293550 A1 * | 12/2007 | Rochling et al. | 514/361 |
| 2013/0065759 A1 * | 3/2013 | Narayanan | C08K 5/17 504/166 |

FOREIGN PATENT DOCUMENTS

WO WO 2008/095794 * 8/2008 ............. A01N 47/34

OTHER PUBLICATIONS

PCT International Search Report PCT/US2011/020679, dated Feb. 25, 2011.

* cited by examiner

*Primary Examiner* — Abigail Vanhorn
(74) *Attorney, Agent, or Firm* — Thompson Hine LLP; William J. Davis

(57) ABSTRACT

A matrix composition capable of forming an emulsion/micro-emulsion comprising an emulsifiable matrix, essentially free of alkyl pyrrolidone and alkoxylated alcohol, comprising:
(i) a long chain substituted amide;
(ii) a surface active agent; and
(iii) optionally, an organic diluent.

6 Claims, No Drawings

MATRIX COMPOSITION FOR DELIVERY OF HYDROPHOBIC ACTIVES

BACKGROUND OF THE INVENTION

The art has described microemulsion concentrates for active ingredients. See, for example, Narayanan U.S. Pat. No. 6,045,816, issued Apr. 4, 2000 "Water-Based Microemulsion of a Pyrethroid"; U.S. Pat. No. 6,187,715, issued Feb. 13, 2001 "Water Based Microemulsions of a Lower Alkyl Ester of Quinoxalinyl Herbicide"; U.S. Pat. No. 6,251,416—issued Jun. 26, 2001 "Water-Based Microemulsion of a Pyrethroid"; U.S. Pat. No. 6,541,516—issued Apr. 1, 2003 "Water Miscible Emulsions of Pyrethroid Insecticides or Triazole Fungicides".

Technical Field of the Invention

The present invention relates to a matrix composition capable of forming an emulsion/micro-emulsion/dispersion comprising an emulsifiable matrix, essentially free of alkyl pyrrolidone and alkoxylated alcohol, comprising: (i) a long chain substituted amide; (ii) a surface active agent; and (iii) optionally, an organic diluent. The matrix composition optionally can further comprise a water insoluble film-forming polymer. More particularly, the present invention relates to the matrix composition which dissolves hydrophobic active to form a concentrate. The concentrate on dilution with water forms an emulsion/micro-emulsion or dispersion.

The hydrophobic active useful in the practice of the invention can be selected from agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, organic solvents and monomers for polymers, and/or disinfectants and/or combinations thereof.

Further, the matrix of the present invention is free of alkyl pyrrolidones and alkoxylated alcohols. The present invention provides a composition that finds application in providing efficient delivery of hydrophobic actives alone or in combination with film forming polymers suitable for film forming applications such as wood protection, plant protection and the like.

Description of the Prior Art

Delivery of hydrophobic actives is always a challenging task. Particularly, hydrophobic actives include herbicides, insecticides, fungicides, light stabilizers, UV absorbers, synthetic hydrocarbons, radical scavengers, resins, natural waxes, fragrances, disinfectants and/or combinations. They are most preferably applied in the form of aqueous emulsions, solutions or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the basic problems in delivering hydrophobic actives is the fact these chemicals often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the actives/chemical itself or to its subsequent application. This toxicity may also be disadvantageous with respect to handling and also may adversely affect the environment.

Another problem is associated with the use of certain types of polymers which exhibit film-forming properties and when dissolved in a solvent, can be applied for the purpose of providing a coating on a substrate. Usually, the film-forming polymer in the solvent is applied to the particular substrate to be coated, and the solvent is allowed to evaporate or removed leaving a film of the polymer. Generally, however, such film-forming polymers are soluble only in organic solvents. The use of such organic solvents generally is undesirable since they exhibit environmentally adverse properties, are often hazardous or flammable, and are generally expensive. In order to avoid the environmentally adverse effects of such organic solvents as well as to reduce the cost involved with using such solvents, rather complicated solvent recovery procedures must be used.

Various attempts are made to provide emulsified or suspension formulations, difficulties are encountered with respect to providing a desirably high concentration of the hydrophobic active ingredients particularly agricultural, herbicides, pesticides etc. Emulsions (or macroemulsions) are usually unstable. The suspended droplets will eventually agglomerate and the dispersed phase will phase separate. Emulsion droplet sizes are much larger, typically one micron or more, resulting in a cloudy or milky dispersion. The nature of an emulsion may depend on the order of mixing of the ingredients and the amount of energy put into the mixing process. The final microemulsion state will not depend on order of mixing, and energy input only determines the time it will take to reach the equilibrium state. There have been limited efforts to develop.

Thus, when such hydrophobically actives/chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants, woods or as coatings.

The development of microemulsion technology has enabled formation of improved dispersions for some materials. Microemulsions are thermodynamically stable dispersions of one liquid phase into another, stabilized by an interfacial film of surfactant. This dispersion may be either oil-in-water or water-in-oil. Microemulsions are typically clear solutions, as the droplet diameter is approximately 100 nanometers or less. The interfacial tension between the two phases is extremely low.

U.S. Pat. No. 5,317,042 disclosed a clear stable, efficacious aqueous microemulsion of a pyrethroid insecticide, alone, or in a complex mixture, obtained by mixing the insecticide with an inert matrix composition containing a defined mixture of nonionic surfactant to form a microemulsion concentrate, and diluting with water. The inert matrix composition consisted of a predetermined mixture of nonionic surfactants which also included nonylphenol ethoxylate with HLB>6. However, the presence of nonylphenol ethoxylate in the formulation may be considered detrimental in some cases.

Further, U.S. Pat. No. 5,425,955 discloses emulsion concentrates of water-insoluble film-forming polymers which can be utilized to form water-resistant films of active ingredients, such as, agriculturally active chemicals. Methods for preparation and use of the emulsion concentrates are disclosed.

Similarly, U.S. Pat. No. 5,766,615 discloses compositions that are composed of the water-insoluble polymers, a surfactant, and a long chain alkylpyrrolidone and which form clear stable microemulsion or solution of the insoluble polymer is obtained on the addition of water.

Most of the prior art cited references suggested the use of alkyl pyrrolidone solvent as one of the major components of the matrix. However, in recent years more stress has been on environmentally safe or EPA approved chemicals that can be safely applied to agricultural fields.

U.S. Pat. No. 5,283,229 discloses the combination of alkyl pyrrolidones and dialkyl amides. The invention particularly relates to a concentrate which is composed of an agriculturally active chemical, a surfactant, and a solvent composed of first and second components. The first component is selected from the group consisting of N-methylpyrrolidone, ethylene carbonate, propylene carbonate, butylene carbonate, N-N,dimethylimidazolone, dimethyl formamide and dimethylacetamide, dimethylsulfoxide, and mixtures thereof and the second component is selected from the group consisting of octylpyrrolidone, dodecylpyrrolidone, N-2-ethylhexylpyrrolidone, and mixtures thereof.

However, the microemulsion concentrates of the above related patents require a large amount of N-alkyl pyrrolidones including N-methyl pyrrolidone for increased loading of the active ingredients. N-methyl pyrrolidone is listed under California Proposition 65 with certain labeling restrictions. Furthermore, the use of the hydrophobic solvents disclosed in U.S. Pat. Nos. 6,541,516 and 6,187,715 limits the type of active ingredients and the loading depending on the solubility of the active ingredients in the hydrophobic solvent chosen.

Other alternatives are cited in U.S. Pat. No. 4,419,282 which discloses a preferred composition containing N-N, dimethylimidazolone, but does not suggest emulsions in water.

US 20060058191 discloses a pesticide composition featuring an alkoxylated alcohol. Alkoxylated alcohols can provide residual alkylene oxide which is undesirable for health and environmental concerns.

However, it is desired to look for options which are environmentally safe and approved and compatible with the actives of interest. A need therefor exists for alternative methods of dispersing of hydrophobic actives and/or water insoluble film forming polymers, which are particularly used in agricultural fields.

Accordingly, it is an object of this invention to provide a matrix composition for new and improved stable microemulsion concentrates which does not require N-alkyl pyrrolidones and/or alkoxylated alcohols in concentrates containing a high loading of different active ingredients. Such compositions are stable upon dilution with water, and which have a relatively long shelf-time, without significant separation or precipitation.

Accordingly, it is one of the objectives of present invention to provide substantially stable homogeneous, water emulsifiable matrix composition which is essentially free of alkyl pyrrolidones and alkoxylated alcohols.

The invention relates to a matrix composition for emulsifiable concentrates containing a desired hydrophobic active or mixtures thereof, and, more particularly, to a matrix with no N-alkyl pyrrolidone including a N,N dialkyl(C1-C4) long chain (C8-C30) acid amide, preferably N,N dialkyl(C1-C2) long chain (C8-C16) acid amide, most preferably N,N dimethyl long chain (C8-C12) acid amide, optional co-solvent like Vegetable oils, ketones, hydrocarbons, esters, ethers, lactones, alcohols, polyols and others capable of solubilizing the active ingredient and preferably with low solubility in water. Additionally, emulsifiers compatible with the solvent system where the chosen emulsifiers are homogeneous with the solvent without any separation during storage under the ambient conditions.

More particularly, the present invention provides an emulsifiable matrix composition for delivery of hydrophobic actives comprising (i) a long chain substituted amide; (ii) a surface active agent; and (iii) optionally, an organic diluent.

The matrix composition of the present invention can be used as a coating for substrates, such as wood, metal, glass, growing crops, soils and the like; as an adjuvant to enhance crop protection and yield and is compatible with several crop protection concentrates especially on dilution in water at use level. The matrix provides a water resistant film on application to surfaces, especially growing crops; rain-fastness during the crop growth; effective enhancement in the crop protection against the pathogen or pests like fungicides and insecticides and herbicides; increased yield of the crop; and is capable of being used as a granulating fluid to produce water-dispersible granules with the adjuvant incorporated.

SUMMARY OF THE INVENTION

In accordance with the present invention, there is provided a clear one phase efficacious aqueous emulsion/microemulsion/dispersion of a hydrophobic active, which is essentially free of alkyl pyrrolidones and alkoxylated alcohols.

More specifically the present invention provides a matrix composition capable of forming emulsion/micro-emulsion/dispersion comprising an emulsifiable matrix, essentially free of alkyl pyrrolidone and alkoxylated alcohol, comprising: (i) a long chain substituted amide; (ii) a surface active agent; and (iii) optionally, an organic diluent.

The straight long chain substituted amide used for the present invention can be a dialkyl acid amide having the formula:

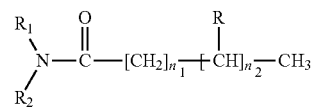

wherein $R_1$ and $R_2$ are lower alkyl with 1-4 carbon atoms, alicyclic or aromatic; $n_1$=0-18, $n_2$=0-18, R=H or $CH_3$, Preferably, R1=R2=CH3; R=H, $n_2$=0; $n_1$=5-11, and more preferably 7-9.

In a preferred embodiment, the dialkyl acid amide is selected from the group consisting of N,N-dimethyl hexamide, N,N-dimethyl octanamide, N,N-dimethyl decanamide, N,N-dimethyl dodecanamide, N—N-dimethyl decamide, N,N-dimethyl tetradecanamide, or combinations thereof.

The surface active agent is derived from food grade material and it include non-ionic or Zwitterionic and/or anionic surfactants well known to those skilled in the art. Occasionally, cationic surfactants such as lecithin may also be used.

In one preferred embodiment, the matrix composition can further comprise a water insoluble film forming polymer. The film-forming polymer can include 1 to 60% by weight of a water-insoluble graft polymer of N-vinylpyrrolidone and an α olefin selected from the group consisting of C16 α-olefins in a 50:50 weight ratio and C20 α-olefins in a 20:80 weight ratio. Preferably, the α-olefin contains from 8 to 30 carbon atoms.

The matrix composition of the present invention can further comprise solvent for the polymer, co-solvents, co-emulsifiers, wetting combinations, ionic emulsifiers, stabilizers, and/or surface active buffers and mixtures thereof.

The present invention also provides a method of preparing a concentrate comprising dissolving 1-50% by weight of one or more of hydrophobic actives in 99-50% of said matrix composition.

The concentrate results in stable emulsion/dispersion when diluted with 10-99 wt. % water containing 0.0005 to 5 wt. % of said hydrophobic actives based on the total diluted matrix composition.

The invention further provides a method for the delivery of hydrophobic actives selected from the group consisting of agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, organic solvents and monomers for polymers, disinfectants and/or combinations.

Another preferred embodiment of the present invention provides a matrix composition essentially free of alkyl pyrrolidone and alkoxylated alcohol comprising, by weight:
(a) 1-99% of a straight long chain substituted amide;
(b) 0-30% of anionic emulsifier;
(c) 0-30% of an ethoxylated/propoxylated (EO/PO) block copolymer as surfactant/stabilizer;
(d) 1-99% of non ionic emulsifier; preferred 20-80%; most preferred 30-70%; and
(e) 0-5% of a surface active acid to produce an appropriate stabilizing pH or a phosphate ester acid as a pH buffer.

In yet another embodiment there is provided a matrix composition comprising:
(a) N,N-dimethyl octanamide, (b) DOSS, (c) Pluronic or Ethox, (d) ethoxylate castor oil and (e) Rhodafac.

The matrix composition of the present invention can be used as a coating for substrates, such as wood, metal, glass, growing crops, soil and the like; as an adjuvant to enhance crop protection and yield and is compatible with several crop protection concentrates especially on dilution in water at use level. The matrix provides a water resistant film on application to surfaces, especially growing crops; rain-fastness during the crop growth; effective enhancement in the crop protection against the pathogen or pests like fungicides and insecticides and herbicides; increased yield of the crop; and is capable of being used as a granulating fluid to produce water-dispersible granules with the adjuvant incorporated.

DESCRIPTION OF PREFERRED EMBODIMENTS

The composition of the present invention is suitable for hydrophobic actives with or without the combination of water insoluble film polymers. The scientists have successfully come up with such an approach which is environmentally safe and at the same time having broad area of applications.

In practice delivering a hydrophobic moiety plays a crucial role, thus a lot of effort is required in terms of performance and safety design of the delivery matrix. The present invention relates to a matrix composition capable of forming emulsion/micro-emulsion/dispersion comprising an emulsifiable matrix, essentially free of alkyl pyrrolidone and alkoxylated alcohol, comprising: (i) a long chain substituted amide; (ii) a surface active agent; and (iii) optionally, an organic diluent.

While applicants do not wish to be bound by any theories, it is believed that the mechanism of enhancement of solubility and stability of the hydrophobic actives is generally attributed to the ability of the straight long chain substituted amides, particularly dimethyl amides, to solublize the hydrophobic active ingredients, due to their hydrophilicity. These long chain amides can be used in higher concentration and can accommodate/load high concentration of the active ingredients. They are also compatible with many other solvents with a wide range of polarity. Another important feature of long substituted amides is their proven environmental safety by various regulatory authorities.

The matrix composition of the present invention is uniquely formulated to provide an efficient clear stable emulsion/micro-emulsion/dispersion of various hydrophobic actives on dilution with water. Further, due to the presence of the optional film former, the solution thus formed, can be utilized to produce films of the particular film forming polymer on a given substrate.

As used herein, the term "micro-emulsion" means an oil-in-water or water-in-oil, transparent thermodynamically stable dispersion of two or more immiscible liquids or a solid in a liquid wherein the dispersed phase consists of small droplets with diameters in the range of about 10 to 100 millimicrons. Such micro-emulsions are clear and appear as a single phase to the naked eye.

As used herein, the term "clear" or "transparent" as applied to a liquid means that the liquid appears as a single phase without any particulate or colloidal material or a second phase being present when viewed by the naked eye.

As used herein, the term "hydrophobic actives" includes compounds/chemicals and mixtures thereof that would normally take the form of water-immiscible or oily liquids and/or solids which are substantially insoluble in water. Such compounds particularly includes agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, disinfectants and/or combinations. The compounds are described/exemplified in detail in U.S. Pat. No. 5,283,229 (ISP).

The hydrophobic actives concentration should be as high as possible so long as it does not precipitate out upon dilution of the concentrate with water for a reasonable period of time and achieves the desired effect. Precipitation (crystal formation) on standing not only depletes the solution of actives, it can also lead to fouling of application equipment, i.e., sprayers, etc. With the present invention, it is possible to obtain concentrates with actives concentrations in excess of about 5 weight percent which form a stable emulsion upon being diluted with water. Preferably, the amount of active is from 5 to 50% and most preferably, 10 to 30%.

The "straight long chain substituted amide" used for the present invention can be a dialkyl acid amide having the formula:

wherein $R_1$ and $R_2$ are lower alkyl with 1-4 carbon atoms, alicyclic or aromatic; $n_1$=0-18, $n_2$=0-18, R=H or $CH_3$, Preferably, $R_1$=$R_2$=$CH_3$; R=H, $n_2$=0; $n_1$=5-11, and more preferably 7-9.

Preferably, the amount of the amide is from about at least about 1 to 99 weight percent, more preferably from about 15 to 45 weight percent, and most preferable from about 25 to 35 weight percent. Also, mixture of these amides may be used.

In a preferred embodiment, the dialkyl acid amide is selected from the group consisting of N,N-dimethyl hexamide (N,N-Dimethyl Caproamide), N,N-dimethyl octanamide (N,N-Dimethyl Caprylamide), N,N-dimethyl decanamide (N,N-Dimethyl Capramide), N,N-dimethyl dodecanamide (N,N-Dimethyl Lauramide), N—N-dimethyl decamide, N,N-dimethyl tetradecanamide (N,N-Dimethyl Myristamide).

These compounds are sold under the trademarks Halcomide by CP Hall. See CP Hall Company, technical bulletin no. 827733 (July, 1974). See also U.S. Pat. No. 3,342,673.

The "water-insoluble polymer" used in the present invention are graft polymer vinylpyrrolidone and α-olefin wherein the N-vinylpyrrolidone is present in more than 20 percent on a weight basis. Preferably, the weight percent of N-vinyl pyrrolidone is at least 50 percent. The α-olefin should contain up to 20 carbon atoms.

Polymers particularly suitable for use in the present invention include polymers, such as, Ganex 516, which is copolymer of an α-olefin and N-vinylpyrrolidone (50/50 percent mixture). Typically, such .alpha.-olefins contain up to 20 carbon atoms and preferably, contain 16. The weight average molecular weight of such polymers is generally greater than about 20,000. Particularly suitable are water-insoluble polymers, such as, Agrimer AL25 (International Specialty Products (ISP) Corporation), which is a copolymer of an .alpha.-olefin having the formula $C_{14}H_{29}CH=CH_2$ (50%) and N-vinylpyrrolidone (50%), and Agrimer AL30 (ISP Corporation), which is a copolymer of an α-olefin having 20 carbon atoms (80%), and N-vinylpyrrolidone (20%). All percents herein are percent by weight based on the total weight of the composition. See also U.S. Pat. No. 5,766,615.

Typically, the composition of the invention comprises from about 0 to 20 weight percent of the water insoluble polymer.

The term "surfactant/emulsifier/surface active agents" used herein refers to surface active agents derived from food grade material and it includes non-ionic/zwitterionic and or anionic surfactants well known to those skilled in the art. The selection is made on a case by case basis in order to optimize the solubility and stability of the emulsion.

Typical non-ionic/zwitterionic surface active agents include edible monoglycerides, diglycerides, poly-glycerol esters, non-ionic phospholipids, non-fatty carboxylic acid esters of fatty acid esters, partial sugar-fatty acid esters, partial fatty acid esters of polyols and mixtures thereof. Alkoxylated versions of the above can also be used.

Suitable anionic surface active agents include lactylated fatty acid salts, anionic phospholipids, anionic non-fatty carboxylic acid esters of fatty acid/esters and their metal salts, fatty acids and their metal salts, alkali metal salts, alkaline metal salts and mixtures thereof, carboxylate salts, sulfates, sulfonates, phosphonates, phosphates, sarcocinates and mixtures thereof. Alkyl, aryl and aralkyl substituted versions of the above and alkoxylated versions of the above also can be used.

The surfactant may be present in amounts from about 1 to 99%, preferably 5 to 50%, and most preferably, from 10 to 20%.

The inventive composition may further comprise an organic diluent which is a synthetic or naturally occurring oil having a high hydrophobic character or having a fractional dispersive solubility parameter of greater than 50% 70% and preferably greater than 85% and a molar volume preferably of greater than 90 $cm^3$/mole. These properties are defined in the C.R.C. Handbook referred to hereinabove.

Typical diluents include alcohols, ethers, esters, ketones, aldehydes, aliphatic and aromatic, and cyclic hydrocarbons, naturally occurring flavoring agents, vegetable oils, flavoring agents, fragrances, and monomers, propylene carbonate, propylene glycol, reduced vinyl pyrrolidone dimer, gamma-butyrolactone, N,N-dimethyl imidazolidone, N,N-dialkyl amide ester with more than 2 carbon, cyclohexanone and methyl ethyl ketone, benzophenone, benzyl benzoate esters of long chain carboxylic acid with greater than 4 carbon atoms or esters with an alkyl group from the alcohol segment has more than 4 carbon atoms, alcohols having greater than six carbons, or hydrocarbon solvents for those active ingredients having high solubility and with low water solubility. Also suitable as the organic diluent are aromatic petroleum oils including those which are commercially available distillates from crude oils having an average boiling point greater than 200° C. Typical of such materials are those sold under the trademarks Exxon 200 or Texaco 400. Of course, such aromatics should be approved for use as a carrier for hydrophobic actives cited herein.

The diluent may be present in amounts of from about 0 to 90%.

In a preferred embodiment, the matrix composition of the present invention is dissolved in one or more of hydrophobic actives to provide a concentrate. The concentrate comprises 1-50% by weight of one or more of hydrophobic actives in 50-99% of said matrix composition. Preferably, the concentrate comprises 5-40% by weight of one or more of hydrophobic actives in 60-95% of said matrix composition. More preferably, the concentrate comprises 10-30% by weight of one or more of hydrophobic actives in 80-90% of said matrix composition.

The concentrate resulted in stable emulsion/micro-emulsion/dispersion when diluted with 10-99 wt. % water containing 0.0005 to 5 wt. % of said hydrophobic actives based on the total diluted matrix composition.

The invention further provides a method for the delivery of hydrophobic actives selected from the group consisting of agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, organic solvents and monomers for polymers, disinfectants and/or combinations.

The matrix composition of the present invention can further comprise solvent for the polymer, co-solvents, co-emulsifiers, wetting combinations, ionic emulsifiers, stabilizers, surface active buffers and mixtures thereof.

In another preferred embodiment of the present invention, there is provided a matrix composition essentially free of alkyl pyrrolidone and alkoxylated alcohol comprising, by weight:
(a) 1-99% of a straight long chain substituted amide; preferred 2-45%; most preferred 5-30%;
(b) 0-30% of anionic emulsifier; preferred 2-25%; most preferred 5-20%;

(c) 0-30% of an ethoxylated/propoxylated (EO/PO) block copolymer as surfactant/stabilizer; preferred 0.75-20%; most preferred 1-15%;
(d) 1-99% of non ionic emulsifier; preferred 20-80%; most preferred 30-70%; and
(e) 0-5% of a surface active acid to produce an appropriate stabilizing pH or a phosphate ester acid as pH buffer; preferred 0.25-4%; most preferred 0.5-3%.

In yet another embodiment there is provided a matrix composition comprising:
(a) N,N-dimethyl octanamide, (b) DOSS, (c) Pluronic or Ethox, (d) ethoxylate castor oil and (e) Rhodafac.

In preferred embodiments, the matrix composition of the present invention can be used as a coating for substrates, such as wood, metal, glass and the like; used as an adjuvant to enhance crop protection and yield is compatible with several crop protection concentrates especially on dilution in water at use level; provides a water resistant film on application to surfaces, especially growing crops; provides rainfastness during the crop growth; provides effective enhancement in the crop protection against the pathogen or pests like fungicides and insecticides and herbicides; provides increased yield of the crop; and capable of being used as a granulating fluid to produce water-dispersible granules with the adjuvant incorporated.

In one of the preferred embodiments, the present composition may preferably be formulated in the form of an emulsion. The emulsion may be, for example, anhydrous, an oil-in-water emulsion, a water-in-oil emulsion, an oil-water-oil emulsion, a water-oil-water emulsion, an oily solution, a lipid fusion, a hydro-alcoholic gel, an anhydrous gel, an aqueous gel, an alcoholic solutions or a hydro-alcoholic solution.

In one embodiment, the compositions prepared with active ingredient produced with water and the sub-micron droplets can be applied as a spray, preferably the aerial spray for mass eradication of parasites such as insects, mosquitoes, flies etc; for example control of West Nile Virus mosquito, and other species.

In yet another embodiment, the compositions made from the matrices of this invention carrying seed protecting components can be used for seed treatment by coating on the seeds aqueous dilutions of the concentrates. The concentrates could be prepared by dissolving the seed protecting compounds in the matrices of this invention.

In one preferred embodiment, the active ingredient is Pine Oil, natural or synthetic. A series of emulsifiable concentrates were prepared at 44% and 20% pine oil concentration for dilution in water. These emulsions were studied for clarity at dilutions in increments of 1/1, 1/16, 1/32, 1/64, and 1/355. These compositions can be used as additives or in cleaning compositions at high dilution with water, or as a softener or as a media to incorporate insect repellants.

EXAMPLES

The compositions shown below were prepared by weighing in appropriate quantities of the ingredients to make up 100 g samples in a 2-ounce stoppered bottle. The contents were dissolved using a rotary shaker over a period of 16 hours. All compositions were homogeneous at room temperature.

Stability evaluation of the samples was carried out as previously described in U.S. Pat. No. 6,045,816. The stability of the concentrates and on dilution is shown below.

The following examples further illustrate the invention.

Example 1

Preparation of Matrix of Invention 100 g matrix composition was prepared by dissolving the following ingredients in a 2-ounce stoppered bottle. 12.5 g Hallcomide M 8-10 (a commercial mixture of N,N dimethyl octanamide and N,N dimethyl decanamide), 74.5 g castor oil ethoxylate (30EO), 11.0 g EO/PO (PEGOL L 31) copolymer, and 2.0 g branched ethoxylated phosphate ester (9-10 EO). The composition was stored at 250 C, 500 C, and 0 C for a period of three weeks and remained clear and also passed three cycles of freeze-thaw test at 250 C-500 C-0 C. On dilution in water including 342 ppm WHO hard water, at 1/200 produced optically clear compositions at room temperature (RT).

Example 2

78.57 g of composition of Example 1 was mixed with 21.43 g of Propylene Carbonate as polar co-solvent to produce a homogeneous solution of the desired matrix composition. On dilution at 1/200 as in Example 1 produced stable optically clear compositions at RT, elevated and reduced temperature.

Example 3

90 g of composition of Example 1 was mixed with 10 g of propylene carbonate to produce essentially similar results as in Example 2.

Example 4

20 g of Permetrin was dissolved in 80 g of the matrix of Example 1 to produce a Permethrin concentrate.

Example 5

20 g of Permetrin was dissolved in 80 g of the matrix of Example 2 to produce a Permethrin concentrate.

Stability of Concentrates

All concentrate compositions shown herein were clear, homogeneous solutions at ambient conditions and at 50° C. and at 0° C., when stored for three weeks. All samples passed the standard freeze thaw cycle three times of alternate storage at 50° C. and 0° C. through room temperature for 24 hours at each temperature without any separation.

Stability on Dilution

Each of the concentrates shown herein were diluted with deionized water as well as 1000 ppm WHO hard water at the rates: 1/200 and any separation was noted by visual observation as a function of time during storage for 30 days at room temperature (22° C.-25° C.) and at 4° C. The results are summarized below in Tables 1, 2, and 3:

All samples at the above dilutions: 1/200 when stored at ambient temperature 22-25° C. were clear, monitored for 30 days of storage.

TABLE 1

Room temperature stability of concentrates and dilutions

| Room Temp | Sample | |
|---|---|---|
| | Example 4 | Example 5 |
| Day 1 | | |
| Concentrate | Clear | clear |
| 1/200 Dilution | Clear | clear |
| Day 15 | | |
| Concentrate | Clear | clear |
| 1/200 Dilution | Clear | clear |
| Day 30 | | |
| Concentrate | Clear | clear |
| 1/200 Dilution | Clear | clear |

TABLE 2

Sub-ambient temperature stability of the concentrate and dilutions

| Temp = 4° C. | Sample | |
|---|---|---|
| | Example 4 | Example 5 |
| Day 1 | | |
| Concentrate | Clear | clear |
| 1/200 Dilution | Clear | clear |
| Day 15 | | |
| Concentrate | Clear Slightly hazy, but reversibly became clear at RT | clear |
| 1/200 Dilution | Clear at RT | clear |
| Day 30 | | |
| Concentrate | Clear | clear |
| 1/200 Dilution | Clear | clear |

TABLE 3

Elevated temperature stability of concentrate and dilutions

| Temp = 45° C. | Sample | |
|---|---|---|
| | Example 4 | Example 5 |
| Day 1 | | |
| Concentrate | Clear | clear |
| 1/200 Dilution | Clear | clear |
| Day 15 | | |
| Concentrate | Clear | clear |
| 1/200 Dilution | Clear | clear |
| Day 30 | | |
| Concentrate | Clear | clear |
| 1/200 Dilution | Clear | clear |

Example 6

Example 2 was repeated except 20 g of Benzyl alcohol was dissolved in 80 g of composition Matrix of Example 1. Diluted solutions of 1/200 was clear. Active ingredients soluble in Benzyl alcohol could be formulated using the above matrix composition, similar to Example 2.

Example 7

Example 6 was repeated except 40 g of Benzyl alcohol was used. Diluted solutions at 1/200 was clear. Active ingredients soluble in Benzyl alcohol could be formulated using the above matrix composition.

Example 8

Example 7 was repeated except 10 g Ethyl Lactate was dissolved in 90 g of composition Matrix of Example 1, to produce a homogeneous solution. On dilution at 1/200 produced optically clear composition.

Example 9

Example 8 was repeated except 30 g of Ethyl Lactate was used to dissolve in 70 g composition Matrix of Example 1 producing essentially same result.

Example 10

Example 9 was repeated except 10 g-40 g of PEG 400 (Polyethylene glycol) was dissolved 90 g-60 g of Composition of Example 1 to produce 100 g of concentrates. Diluted solutions of 1/200 were optically clear.

Example 11

Example 10 was repeated except 10-40 g of N methyl pyrrolidone was used in the place of PEG 400 producing essentially similar results.

Example 12

Example 11 was repeated except 20-40 g of Isopropyl alcohol was dissolved in 80-60 g of Composition of Example 1 to produce 100 g concentrates. Diluted solutions of 1/200 were clear.

Example 13

Example 12 was repeated except 10 g THF (tetrahydrofuran) was used to dissolve in 90 g composition of Example 1 to produce 100 g homogeneous composition. On dilution at 1/200 in water produced optically clear composition.

Example 14

Example 13 was repeated except 40 g THF was used along with 60 g composition of Example 1, producing essentially the same result.

Example 15

Example 14 was repeated except 10-30 g Solvasso 150 (Petroleum distillate hydrocarbon mix) was dissolved in 90-70 g composition of Example 1 to produce 100 g stable concentrates and produced similar results on dilution in water.

Example 16

10 g Propylene Carbonate and 10 g of Permethrin were dissolved in 80 g of Composition of Example 1, This concentrate was diluted to 1/200 to produce optically clear composition. This composition can be used similar to Examples 4 and 5 for termite control in construction sites and in consumer applications. The Propylene carbonate can also be replaced with other polar solvents like N methyl pyrrolidone or similar polar solvents like ester dialkyl amides (Rhodiasolve® Polarclean).

Example 17

Matrix Preparation with 20% Pine Oil

A 20% by weight solution of Pine oil was prepared by weighing 6 grams of Pine Oil, 4 gram of DOSS (Sodium dioctyl sulfosuccinatc) and 20 gram of composition of Example 1 (Matrix-1). This composition was designated as Example 17A. A second composition was prepared following the same procedure using 6 grams Pine Oil, 4 grams DOSS and 20 grams of Matrix-17.2 (comprising 12.4% Hallcomid M-8-10, 76.6% Ethox CO-30, 11% Pluronic L-31). This composition was designated as Example 17B.

Both concentrates were transferred onto a rotary wheel for overnight mixing. The resulting formulations formed clear solutions (each formulation contained 20% Pine Oil, 13.3% DOSS, and 66.6% Matrix 1 or 17.2). These concentrates were diluted with deionized water to various dilutions (from 1/1 to 1/16 ratio) as described in Table 4.

TABLE 4

20% Pine Oil Concentrates and Stabilty on Dilution

| % PO in Matrix | Dilution | Formulation-17A | Formulation-17B | |
|---|---|---|---|---|
| 20% PO with 13.3% DOSS | As is | Matrix with Hallcomide | Matrix with Hallcomide No buffer | |
| | | NTU | NTU | observation |
| | 1/1 | 433 | 327 | Gel |
| | 1/2 | 165 | 18(two layer) | gel |
| | 1/3 | 11.5 | 95.7 | gel |
| | 1/4 | 3.7 | 4.5 | clear |
| | 1/5 | 3.2 | 4.0 | clear |
| | 1/6 | 2.9 | 3.5 | clear |
| | 1/8 | 2.8 | 2.7 | clear |
| | 1/16 | 2.1 | 2.7 | clear |
| | 1/32 | 0.87 | 0.37 | clear |

Testing for clarity: Diluted samples were placed on a rotary wheel for 20 minutes prior to haze measurement. Haze measurements were carried out with Hatch 2100N turbidity meter.

Results: A 1:1, 1:2 and 1:3 ratio of formulated 20% Pine Oil in both matrices diluted with water (10%, 6,7% active Pine Oil, respectively) were found to be homogeneously viscous gel. At dilution ratio of 1/4 and higher all the formulations investigated were clear and flowable with NTU values of 4.7 and lower.

Example 18

Matrix Preparation With 44% Active Pine Oil:

A 44% by weight solution of Pine oil was prepared by weighing 22 grams of Pine Oil, 6.5 grain of DOSS and 22.5 gram of composition of Example 1. This composition was designated as Example 18 A. A second concentrate with 44% Pine Oil was prepared following the same procedure using 22 grams Pine Oil, 6.5 grams DOSS and 22.5 grams Matrix-2 [comprises 12.4% Hallcomid M-8-10, 76.6% Ethox CO-30, 11% Pluronic L-31]. This composition was designated as Example 18B. Both concentrates were transferred onto a rotary wheel for overnight mixing. The resulting formulations formed clear solutions (each formulation contained 20% Pine Oil, 13.3% DOSS, and 66.6% Matrix 1 or 2). These concentrate were diluted with deionized water to various dilutions (from 1/1 to 1/64 ratio) as described in Table 5.

TABLE 5

44% Pine Oil Concentrates and Stability on Dilution

| % PO in Matrix | Dilution | Formulation-7 | Formulation-8 | Dilution |
|---|---|---|---|---|
| 44.4% PO with 11% DOSS | As is | NTU | NTU | observation |
| | 1/1 | 14.4 | 19.4 | gel |
| | 1/2 | 3360 | >9999 | cloudy |
| | 1/3 | 13.3 | 61.4(hazy) | clear |
| | 1/4 | 15.6 | 21.4 | clear |
| | 1/5 | 23.7 | 20.2 | clear |
| | 1/6 | 71.6 | 37.2 | clear |
| | 1/8 | 40.0 | 30.9 | clear |
| | 1/16 | 26.6 | 23.5 | clear |
| | 1/32 | 18.8 | 17.2 | clear |
| | 1/64 | 11.1 | 10.1 | clear |

Testing for clarity: Diluted samples were placed on a rotary wheel for 20 minutes prior to haze measurement. Haze measurements were carried out with Hatch 2100N turbidity meter.

Results:

At 44% pine oil in the concentrates a clear, single phase, liquid was obtained in all formulations. At a dilution ratio of 1:1 with water (22% active Pine Oil) it was a homogeneously viscous solution (clear gel) with haze value of around 15 NTU. At this dilution a gradual separation to two phases over a period of two weeks was found. Maximum haze was exhibited at 1:2 dilution ratio followed by gradual decrease in haze with further dilution (1:3 ratio and higher) as shown in Table 5.

Example 19

100 g matrix composition was prepared by dissolving the following ingredients in a 2-ounce stoppered bottle. 14.5 g Hallcomide M 8-10 (a commercial mixture of N,N dimethyl octanamide and N,N dimethyl decanamide), 86.5 g castor oil ethoxylate (30EO). This was designated as Matrix 119M. In a separate bottle 21 g Pine Oil was mixed with 6.5 g DOSS to produce a homogeneous solution, followed by addition of 22 g of Matrix 19M to form a 50 g homogeneous concentrate.

On dilution in water at levels: 1/4, 1/8, 1/16, 1/32, and 1/64 produced essentially optically clear compositions.

The invention has been described in detail with particular reference to preferred embodiments thereof, but it will be understood that variations and modifications can be effected within the spirit and scope of the invention.

We claim:

1. A matrix composition capable of forming an emulsion, a microemulsion, or a dispersion comprising an emulsifiable matrix, consisting of:

(i) a dialkyl acid amide having the formula:

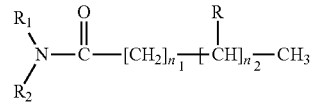

wherein,

R$_1$ and R$_2$ are lower alkyl with 1-4 carbon atoms, alicyclic or aromatic;

n$_1$=0-18, n$_2$=0-18, and R=H or CH$_3$; and (ii) one or more surface active agents, wherein the only surface active agents present are selected from the group consisting of ethoxylated castor oil, ethoxylated/propoxylated block copolymer, ethoxylated phosphate ester, sodium dioctyl sulfosuccinate, and poly(ethylene glycol)-block-poly(propylene glycol)-block-poly(ethylene glycol), and wherein at least one of the surface active agents is ethoxylated castor oil.

2. The matrix composition according to claim 1, wherein R$_1$=R$_2$=CH$_3$; R=H; n$_2$=0 and n$_1$=5-11.

3. The matrix composition according to claim 2, wherein R1=R2=CH$_3$; R=H; n$_2$=0 and n$_1$=7-9.

4. The matrix composition according to claim 1, wherein the dialkyl acid amide is selected from the group consisting of N,N-dimethyl hexamide, N,N-dimethyl octanamide, N,N-dimethyl decanamide, N,N-dimethyl dodecanamide, and N,N-dimethyl tetradecanamide.

5. The matrix composition according to claim 1 having, by weight:

1-99% of the dialkyl acid amide; and 1-99% of the surface active agents, and wherein at least one of the surface active agents is ethoxylated/propoxylated block copolymer.

6. The matrix composition according to claim 5, wherein the dialkyl acid amide is N, N-dimethyl octanamide, and the surface active agents are sodium dioctyl sulfosuccinate, ethoxylated/propoxylated block copolymer, and the ethoxylated castor oil.

* * * * *